(12) United States Patent
Arnholt et al.

(10) Patent No.: US 7,682,202 B2
(45) Date of Patent: Mar. 23, 2010

(54) CONNECTOR ASSEMBLY FOR IMPLANTABLE DEVICE

(75) Inventors: Devon N. Arnholt, Minneapolis, MN (US); Michelle L. Harren, Kirkland, WA (US); Benjamin R. Fruland, Plymouth, MN (US); David J. Hansen, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 509 days.

(21) Appl. No.: 11/261,046

(22) Filed: Oct. 28, 2005

(65) Prior Publication Data
US 2007/0099518 A1    May 3, 2007

(51) Int. Cl.
*H01R 24/00* (2006.01)
(52) U.S. Cl. .................................................... 439/675
(58) Field of Classification Search .............. 439/675, 439/462, 668–669, 219, 352, 909; 607/36–37, 607/116
See application file for complete search history.

(56) References Cited

U.S. PATENT DOCUMENTS

| 5,012,807 | A | | 5/1991 | Stutz, Jr. | |
| 5,261,395 | A | * | 11/1993 | Oleen et al. | 607/15 |
| 5,843,141 | A | | 12/1998 | Bischoff et al. | |
| 6,208,900 | B1 | | 3/2001 | Ecker et al. | |
| 6,643,550 | B2 | | 11/2003 | Westlund et al. | |
| 6,895,276 | B2 | * | 5/2005 | Kast et al. | 607/37 |
| 6,912,423 | B2 | | 6/2005 | Ley et al. | |
| 7,083,474 | B1 | * | 8/2006 | Fleck et al. | 439/668 |
| 7,133,722 | B2 | * | 11/2006 | Hansen et al. | 607/37 |
| 7,167,749 | B2 | * | 1/2007 | Biggs et al. | 607/36 |
| 2004/0034393 | A1 | | 2/2004 | Hansen et al. | |
| 2004/0210268 | A1 | * | 10/2004 | Stubbs | 607/36 |
| 2006/0015150 | A1 | * | 1/2006 | Rusin et al. | 607/36 |

OTHER PUBLICATIONS

"Frequently Asked Questions regarding Connector Task Force", *NASPE, Association for the Advancement of Medical Instrumentation. Pacemaker Committee, Connector Task Force*, PAC/CTF-N248, May 2002; 2 pgs.
"Proposed IS-4 Quadripolar Lead Connector Standard" *AAMI Connector Task Force Proposal for AAMI Work Item PC-73*, May 2002, 2 pgs.

* cited by examiner

*Primary Examiner*—Jean F Duverne
(74) *Attorney, Agent, or Firm*—Schwegman, Lundberg & Woessner, P.A.

(57) ABSTRACT

A header for an implantable pulse generator includes a header body having a bore formed therein, at least one header contact located within the bore to contact a corresponding contact of a lead terminal inserted in the bore, and a rigid component located within the bore.

20 Claims, 3 Drawing Sheets

CONNECTOR ASSEMBLY FOR IMPLANTABLE DEVICE

FIELD OF THE INVENTION

This invention relates to the field of implantable devices, and more specifically to a connector assembly for an implantable device.

BACKGROUND

Leads implanted in or about the heart have been used to reverse certain life threatening arrhythmia, or to stimulate contraction of the heart. Electrical energy is applied to the heart via electrodes on the leads to return the heart to normal rhythm.

A header on an implantable device is used to couple a conductor of a lead with the implantable device. For instance, a connector assembly in the header is used to couple a cardiac stimulator system such as a pacemaker, an anti-tachycardia device, a cardiac heart failure device, a cardioverter or a defibrillator with a lead having an electrode for making contact with a portion of the heart. The lead is typically coupled to the header using a set-screw to stabilize the lead.

SUMMARY

In one example, a header for an implantable pulse generator includes a header body having a bore formed therein, at least one header contact located within the bore to contact a corresponding contact of a lead terminal inserted in the bore, and a rigid component located within the bore to at least partially surround the lead terminal.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
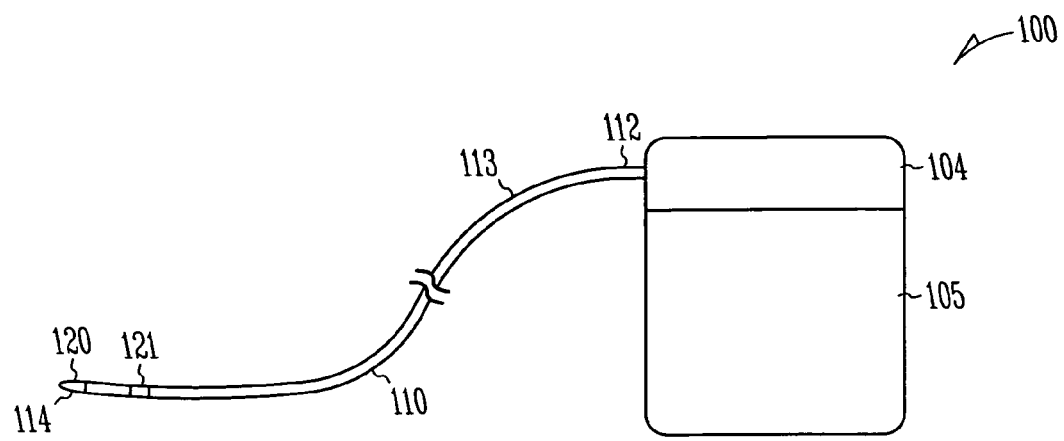
FIG. 1 shows a view of an implantable system according to at least one embodiment.

FIG. 1 shows an implantable system 100, in accordance with one embodiment. System 100 includes a pulse generator 105 and at least one lead 110. The pulse generator 105 includes a source of power as well as an electronic circuitry portion, and has a header 104. The pulse generator 105 includes a battery-powered device which generates a series of timed electrical discharges or pulses. The pulse generator 105 is generally implanted into a subcutaneous pocket made in the wall of the chest. Alternatively, the pulse generator 105 is placed in a subcutaneous or submuscular pocket made in the abdomen, or in other locations. Pulse generator 105 can include a power supply such as a battery, a capacitor, and other components housed in a case. The device can include microprocessors to provide processing, evaluation, and to determine and deliver electrical shocks and pulses of different energy levels and timing for defibrillation, cardioversion, and pacing to a heart in response to cardiac arrhythmia including fibrillation, tachycardia, heart failure, and bradycardia.

Lead 110 includes a lead body 113 having a proximal end 112, where the lead is coupled at the header 104 of pulse generator 105, as further discussed below. The lead 110 extends to a distal end 114, which is coupled with a portion of a heart, when implanted. In one embodiment, the distal end 114 of the lead 110 includes one or more electrodes 120, 121 which electrically couple the lead 110 with a heart. In other examples, electrodes can be located medially or at other locations along the lead. At least one electrical conductor is disposed within the lead 110 and extends from the proximal end 112 to the electrode(s) 120, 121. The electrical conductors carry electrical current and pulses between the pulse generator 105 and the electrode(s) 120, 121.

In other embodiments, system 100 is suitable for use with implantable electrical stimulators, such as, but not limited to, pulse generators, neuro-stimulators, skeletal stimulators, central nervous system stimulators, or stimulators for the treatment of pain.

Figure 2:
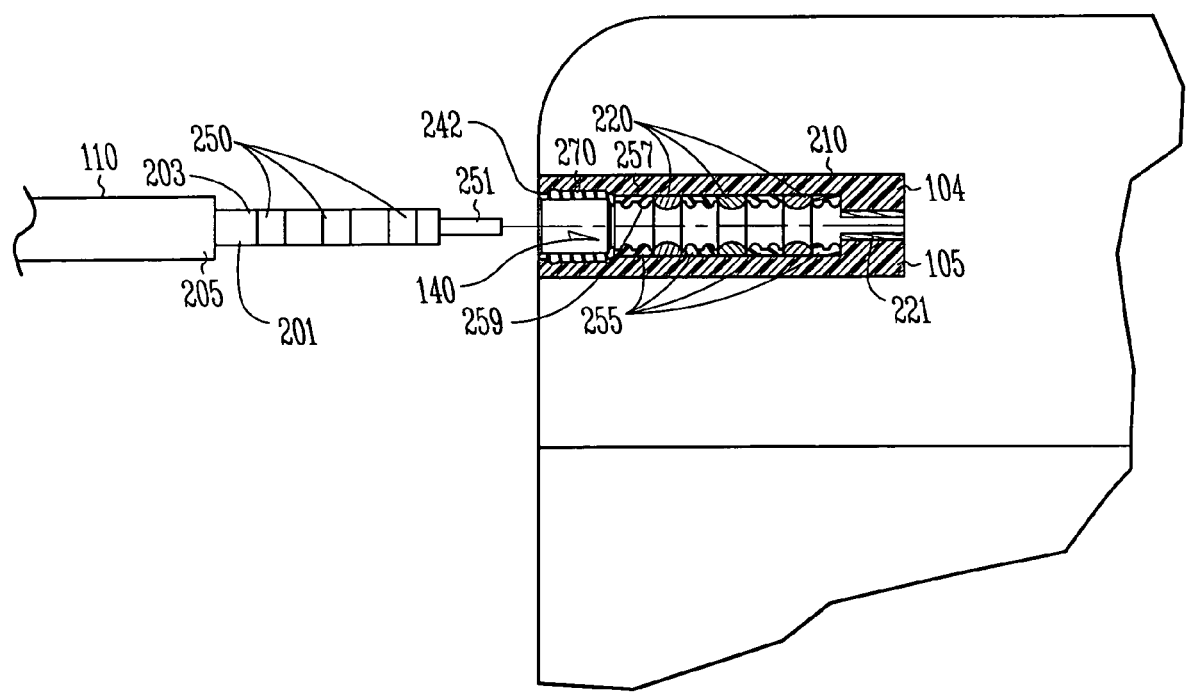
FIG. 2 shows a cross-section side view of a header of the implantable device of FIG. 1.

FIG. 2 illustrates a side section view of header 104, in accordance with one embodiment. The header 104 includes one or more longitudinal bores 140 that are configured to receive a lead terminal 201 of lead 110. In this example, lead terminal 201 is a quadripolar connector. In one embodiment, lead terminal 201 includes three terminal ring contacts 250 and one pin contact 251 spaced along a lead connector pin 203 and electrically insulated from one another. Other examples utilize fewer or more contacts. Lead terminal 201 further includes connector grip sleeve portion 205. Terminal ring contacts 250 can include quadripolar terminal rings or other terminal contact designs. Terminal ring contacts 250 are typically made of stainless steel, titanium, or MP35N. Each terminal ring 250, and pin contact 251, is coupled via a conductor to at least one electrode disposed on lead 110. In some examples, a lead can further include sealing rings.

In one embodiment, header 104 generally includes a header body 210 having the longitudinal bore 140 formed therein and one or more electrical contacts 220, 221 located within the bore 140 to contact corresponding contacts 250, 251 respectively, of lead 110. Contacts 220, 221 are electrically connected to the electronics in pulse generator 105. In some embodiments, header 104 can include a molded plastic and bore 140 can be molded within body 210 and sized to receive terminal 201. In some examples, the bore can include one or more decreasing diameter sections defining a series of steps, with one or more contacts 220 located within each step. Likewise, the terminal 201 can include a stepped design with one or more decreasing diameter portions with one or more contacts 250 on each section.

In one embodiment, header 104 includes seals 255 located within the bore 140 and located between each of the at least one header contacts 220, 221. Seals 255 can be elastomeric tubular members having ribs, or projections, on an inner and outer surface. For example, exterior projections 257 cooperate with the bore to create a fluid seal, and inward projections 259 cooperate with the outer diameter of the lead connector pin 203 to inhibit passage of fluids.

In one embodiment, header contacts 220, 221 can include spring contacts, such as leaf springs, curl springs or coil springs. For example, the electrical contacts 220, 221 can be formed of an MP35N metal alloy material. The contacts 220 include an inner diameter smaller than the outer diameter of the lead terminal ring contacts 250. The springs of contacts 220 are therefore radially deflected when the terminal 201 is inserted through the contacts 220. This causes the contacts 220 to deflect upon insertion of terminal 201 and thereby exert a radial force on the lead ring contacts 250 to maintain electrical contact. In some embodiments, two or more contacts 220 are located within the bore 140. Other embodiments can include fewer or more contacts. In some examples, the contacts 220 can be inserted radially into the header such as discussed in co-pending, co-assigned U.S. application Ser. No. 10/222,151, filed Aug. 16, 2002, which is incorporated herein by reference.

In one embodiment, header 104 includes a rigid component 270 located within bore 104. Rigid component 270 provides support and stabilization for lead terminal 201 so that the lead terminal does not move radially relative to the contacts 220 of header 104. For example, after terminal 201 is inserted, the terminal can be exposed to forces that tend to make the terminal pin move towards the contacts. However, too much relative motion could potentially occur between a lead terminal and a spring contact, for example, and then possibly cause contact resistance instability and spring damage or seal damage.

Rigid component 270 is rigid enough to limit relative motion between the lead terminal 201 and the header contacts 220 and the seals 255. This helps to limit movement between the lead terminal 201 and the seals 255, thereby helping to provide sealing integrity and minimizing damage to the seals either during implant or when implanted. Moreover, stabilizing the lead terminal 210 utilizing rigid component 270 potentially facilitates the use of spring contact 220 designs that would not be acceptable otherwise due to contact resistance instability or susceptibility to damage. This creates more design options for the spring contacts and can lead to a lower cost, and can provide a more robust header.

In this example, component 270 is axially loaded into the lumen of bore 140 at an open front end 242 of the bore. Component 270 can be made of a rigid material, such as a machined or injection molded hard plastic. In some embodiments, the component can be made of a hard ceramic material or a metal material. Other materials can be used if they are rigid enough to limit relative motion between the lead terminal 201 and the header contacts 220 and the seals 255. In one example, rigid component 270 is at least as rigid as lead terminal 201 so as to keep the lead terminal in a relatively fixed position relative to the header.

Figure 3:
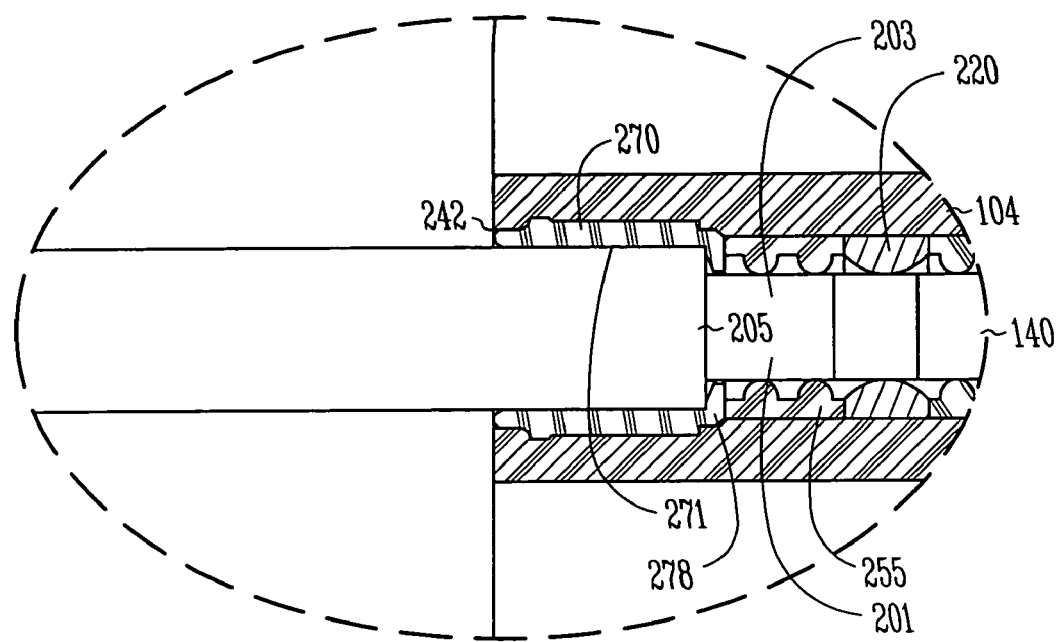
FIG. 3 shows a close-up view of a portion of the header of FIG. 2.

FIG. 3 shows a cross-section view of lead terminal 201 inserted into bore 140 of header 104. The inner diameter surface 271 of component 270 contacts or is in close proximity to lead terminal 201 along substantially the entire surface of connector head portion 205. Component 270 further includes a lip 278 that contacts or is in close proximity to the outer surface of terminal pin 203 of lead terminal 201. This close fit around the surfaces of the lead terminal 201 by rigid component 270 stabilizes the lead terminal 201 by limiting relative motion between the lead terminal and the header contacts.

Rigid component 270 constrains relative motion between the lead and the header thus reducing the risk of contact resistance instability and sealing breaches, for example. It further creates an improved electrical interface between the lead terminal and the pulse generator. The present lead stabilization technique is simple and cost-effective without requiring further actuation by the physician (e.g. set-screws). No mechanical actuation by the physician is needed outside of normal lead insertion. However, in some embodiments, the device can include an optional set-screw to help hold the lead terminal in place within the header 104.

Rigid component 270 also improves alignment of the lead terminal 201 with header 104 during insertion of the lead by constraining the possible angles of approach of the lead terminal 201 as it enters the header. This further reduces risk of damage to spring contacts 220 and reduces risk of damage to header seals 255.

Figure 4:
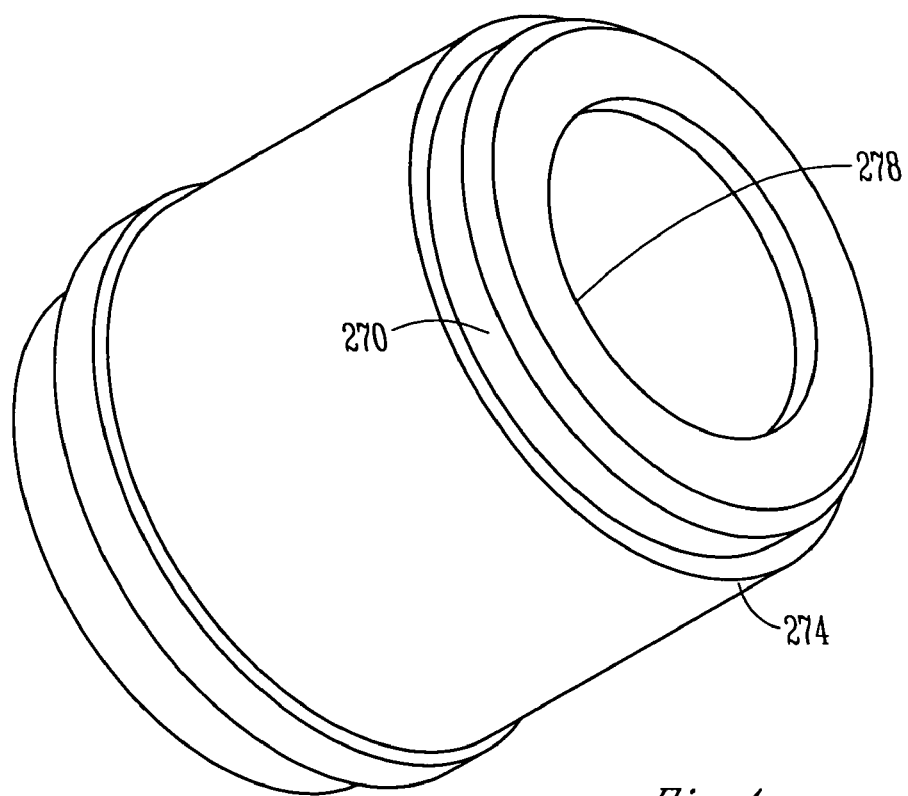
FIG. 4 shows a perspective view of a component for a header, in accordance with at least one embodiment.
Figure 5:
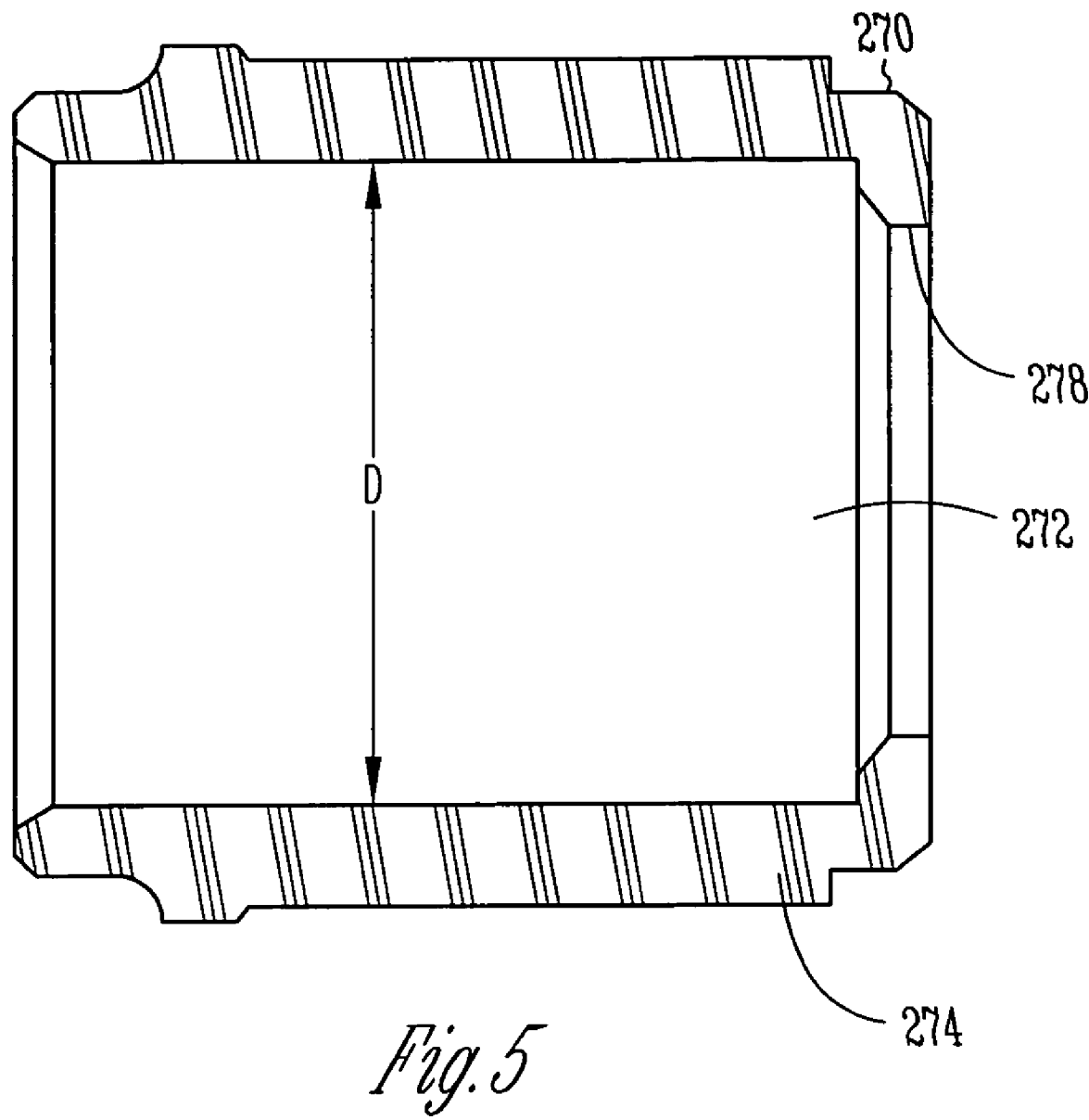
FIG. 5 shows a cross-section view of the component of FIG. 4.

FIG. 4 shows a perspective view of component 270, in accordance with one embodiment. FIG. 5 shows a cross-section view of component 270. Referring also to FIGS. 2 and 3, in one embodiment, rigid component 270 includes a generally cylindrical body 274 having a first inside diameter D and lip 278 at one end of the cylindrical body 274 defining a diameter smaller than the first inside diameter, D. Rigid component 270 also includes a hole 272 therethrough, the hole 272 is dimensioned large enough to allow the lead terminal 201 to pass through but small enough to support the lead terminal 201. In other embodiment, the shape of component 270 can be a partial cylinder and only some surfaces of the component 270 support and contact the lead terminal to restrict radial motion of the lead terminal relative to the header contacts.

Accordingly, in one embodiment a rigid component 270 can be axially loaded into a bore 140 of a header 104. As a lead terminal 201 is inserted into the header, the outer surfaces of the lead terminal are supported by the rigid component 270 to restrict radial motion of the lead terminal relative to the header.

In various embodiments, component 270 can be used for a variety of applications including a header for an IS-1 standard type lead connector, a header for a quadripolar lead connector, and a header for a LV-1 type lead connector, for example.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A header for an implantable pulse generator, the header comprising:
   a header body having a bore formed therein;
   at least one header contact located within the bore to contact a corresponding contact of a lead terminal inserted in the bore; and
   a rigid component located within the bore to at least partially surround a connector head portion of the lead terminal, wherein the rigid component has a length such that the rigid component is positioned within the header bore from an open front end of the bore to the front end of the connector head portion of the lead terminal so as to contact and support the connector head portion of the lead terminal along its entire length within the header bore.

2. The header of claim 1, wherein the at least one header contact includes a spring contact.

3. The header of claim 1, further including elastomeric seals located within the bore and located between each of the at least one header contacts.

4. The header of claim 1, wherein the rigid component is located at an open front end of the bore.

5. The header of claim 1, wherein the rigid component includes a cylindrical shape which surrounds the lead terminal so as to contact an outer surface of the connector head portion of the lead terminal to restrict motion of the lead terminal relative to the at least one header contact.

6. The header contact of claim 1, wherein the rigid component includes a hole therethrough, the hole dimensioned large enough to allow the lead terminal to pass through but small enough to support the connector head portion of the lead terminal.

7. The header contact of claim 1, wherein the rigid component includes a generally cylindrical body having a first inside diameter and a lip at one end of the cylindrical body, the lip defining a diameter smaller than the first inside diameter.

8. A header for an implantable pulse generator, the header comprising:

a header body having a bore formed therein; and at least one header contact located within the bore to contact a corresponding contact of a lead terminal inserted in the bore;

a component located within the bore, the component including an inner diameter dimensioned to limit movement of a connector head portion of the lead terminal and for limiting relative motion between the lead terminal and the at least one header contact, wherein the component has a length such that the component is positioned within the header bore from an open front end of the bore to the front end of the connector head portion of the lead terminal so as to contact and support the connector head portion of the lead terminal along its entire length within the header bore.

9. The header of claim 8, wherein component includes a rigid component located at an open front end of the bore.

10. The header contact of claim 9, wherein the rigid component includes a hole therethrough, the hole dimensioned large enough to allow the lead terminal to pass through but small enough to support the connector head portion of the lead terminal.

11. The header contact of claim 9, wherein the rigid component includes a generally cylindrical body having a first inside diameter and a lip at one end of the cylindrical body defining a diameter smaller than the first inside diameter.

12. A header for an implantable pulse generator, the header comprising:

a header body having a bore formed therein; and at least one header contact located within the bore to contact a corresponding contact of a lead terminal inserted in the bore, the at least one header contact including a spring contact; and a rigid cylindrical component located within the bore at an open front end of the bore, the rigid cylindrical component including a hole therethrough defining an inner diameter, the diameter dimensioned to contact an outer surface of a connector head portion of the lead terminal, wherein the rigid cylindrical component has a length such that the rigid cylindrical component is positioned within the header bore from the open front end of the bore to the front end of the connector head portion of the lead terminal so as to contact and support the connector head portion of the lead terminal along its entire length within the header bore.

13. The header of claim 12, wherein the hole is dimensioned large enough to allow the lead terminal to pass through but small enough to support the connector head portion of the lead terminal.

14. The header of claim 12, further including elastomeric seals located within the bore and located between each of the at least one header contacts.

15. The header of claim 12, wherein the rigid component is adapted to stabilize the lead terminal.

16. The header contact of claim 12, wherein the rigid component includes the inner diameter and a lip at one end defining a diameter smaller than the inner diameter, the lip diameter dimensioned to support a connector pin portion of the lead terminal.

17. The header of claim 12, wherein the rigid cylindrical component is rigid enough to limit relative motion between the lead terminal and the at least one header contact.

18. The header of claim 12, wherein the rigid cylindrical component is at least as rigid as the connector head portion of the lead terminal.

19. The header of claim 12, wherein the rigid cylindrical component includes a hard plastic material.

20. The header of claim 12, wherein the rigid cylindrical component includes a ceramic material.

* * * * *